(12) United States Patent
Clagett

(10) Patent No.: US 11,194,173 B2
(45) Date of Patent: Dec. 7, 2021

(54) NOSE PROTECTION APPARATUS AND METHODS

(71) Applicant: Suzanne Clagett, Saratoga Springs, NY (US)

(72) Inventor: Suzanne Clagett, Saratoga Springs, NY (US)

(*) Notice: Subject to any disclaimer, the term of this patent is extended or adjusted under 35 U.S.C. 154(b) by 275 days.

(21) Appl. No.: 16/443,860

(22) Filed: Jun. 17, 2019

(65) Prior Publication Data

US 2019/0302476 A1 Oct. 3, 2019

(51) Int. Cl.
*G02C 5/12* (2006.01)
*A61F 9/02* (2006.01)
*G02C 5/02* (2006.01)

(52) U.S. Cl.
CPC ............... *G02C 5/12* (2013.01); *A61F 9/026* (2013.01); *A61F 9/029* (2013.01); *G02C 5/02* (2013.01); *G02C 2200/08* (2013.01); *G02C 2200/16* (2013.01)

(58) Field of Classification Search
CPC .......... G02C 5/12; G02C 5/126; G02C 5/02; G02C 2200/08; G02C 2200/16; A61F 9/02; A61F 9/029; A61F 9/026; A61F 5/08
USPC ........... 351/136, 137, 138, 139; 128/200.24; 606/204.45, 5, 6, 199
See application file for complete search history.

(56) References Cited

U.S. PATENT DOCUMENTS

| 4,704,015 | A | 11/1987 | Grendol et al. |
| 4,707,089 | A | 11/1987 | Danloup et al. |
| 4,818,092 | A * | 4/1989 | Bononi ............... G02C 5/00 351/136 |
| 5,976,173 | A | 11/1999 | Berke |
| 6,532,598 | B1 | 3/2003 | Cardarelli |
| 8,062,329 | B2 | 11/2011 | Ierulli |
| 2015/0362745 | A1 | 12/2015 | Hamilton et al. |
| 2019/0302476 | A1 | 10/2019 | Clagett |

FOREIGN PATENT DOCUMENTS

JP 2001/142030 A 5/2001

OTHER PUBLICATIONS

Boomerang Gel Pad for CPCP/BiPAO Masks (CPAPXCHANGE).
(Continued)

*Primary Examiner* — Hung X Dang
(74) *Attorney, Agent, or Firm* — Jay R. Yablon

(57) ABSTRACT

A nose protection apparatus and related methods, for protecting a human nose from prolonged eyewear contact, the apparatus comprising: a center bridge region and two outer protective regions joined by the center bridge region, fabricated from a silicone material into an integral unit; a nasal bridge clearance cutout beneath the center bridge region; omitting any added adhesives, wherein all adhesion properties of the apparatus are inherent to material properties of the silicone material; omitting any structural elements for straightening the apparatus for widening a user's nostrils; a width selected from the width group consisting of: an adult width from 1.2" to 2.8"; and a child width from 0.6" to 1.4"; a height selected from the height group consisting of: an adult height from 0.375" to 0.875"; and a child height from 0.1875" to 0.4375"; a thickness from 0.02" to 0.05"; and a durometer hardness from 5 to 20.

24 Claims, 1 Drawing Sheet

(56) References Cited

OTHER PUBLICATIONS

International search report and written opinion of ISA/US, dated Apr. 21, 2020, for counterpart application PCT/US20/13780.
https://www.breatheright.com/how-to-breathe-better/how-breathe-right-nasal-strips-work.html, printed Jun. 16, 2019.
International Search Report and Written Opinion of the International Searching Authority dated Apr. 21, 2020, for counterpart application PCT/US20/13780.
International Preliminary Report on Patentability dated Apr. 21, 2020, for counterpart application PCT/US20/13780.

* cited by examiner

NOSE PROTECTION APPARATUS AND METHODS

BACKGROUND OF THE INVENTION

It is a common problem that people who wear glasses/eyewear regularly, develop markings or indentations on their skin enveloping the nasal bones in the area above the nasal septum due to prolonged pressure from the eyewear contact components, specifically nose pads, bridge and/or frame against the nose. For many, this is regarded as unsightly, uncomfortable, sometimes painful, and something to be avoided, if possible. One solution is to wear contact lenses in lieu of glasses, but these have their own problems, including for some people, eye irritation. Also, some types of glasses, for example, sunglasses or safety glasses have to be worn as glasses, not contacts.

Although the prior art reveals other products worn or adhered over parts of the nose for other issues and with various material configurations, e.g., snore strips, CPAC mask cushions and nose guard/sun protectors, none of the prior art is specifically configured, as a whole, to take on the unique problem of protecting the skin around the nasal bone/or nose bridge from these adverse effects of prolonged wearing of glasses. With snore strips in particular, which are included in an information disclosure being filed with this application, adhesives ("the underside is 3M adhesive") which are used in combination with rigid ribs ("spring-like-bands") inside the strips pull apart the nostrils ("lift the sides of the nose and open the nasal passages"), and so although serving their purpose of reducing snoring, have the adverse side effect of damaging the skin outside the nose.

The prior art to address these physical impacts of eyewear, such as it is, appears confined to improvements to the nose pads and attachments of the glasses themselves.

It would be desirable to have an apparatus and associated methods of manufacture and use specifically designed to protect the nose from the adverse physical effects of prolonged wearing of glasses/eyewear, which is independent of the eyewear itself.

Moreover, it would be desirable for this apparatus and associated methods not to cause skin damage or irritation.

SUMMARY OF THE INVENTION

A nose protection apparatus and related methods, for protecting a human nose from prolonged eyewear contact, the apparatus comprising: a center bridge region and two outer protective regions joined by the center bridge region, fabricated from a silicone material into an integral unit; a nasal bridge clearance cutout beneath the center bridge region; omitting any added adhesives, wherein all adhesion properties of the apparatus are inherent to material properties of the silicone material; omitting any structural elements for straightening the apparatus for widening a user's nostrils; a width selected from the width group consisting of: an adult width from 1.2" to 2.8"; and a child width from 0.6" to 1.4"; a height selected from the height group consisting of: an adult height from 0.375" to 0.875"; and a child height from 0.1875" to 0.4375"; a thickness from 0.02" to 0.05"; and a durometer hardness from 5 to 20.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) summarized below.

DETAILED DESCRIPTION

Figure 1:
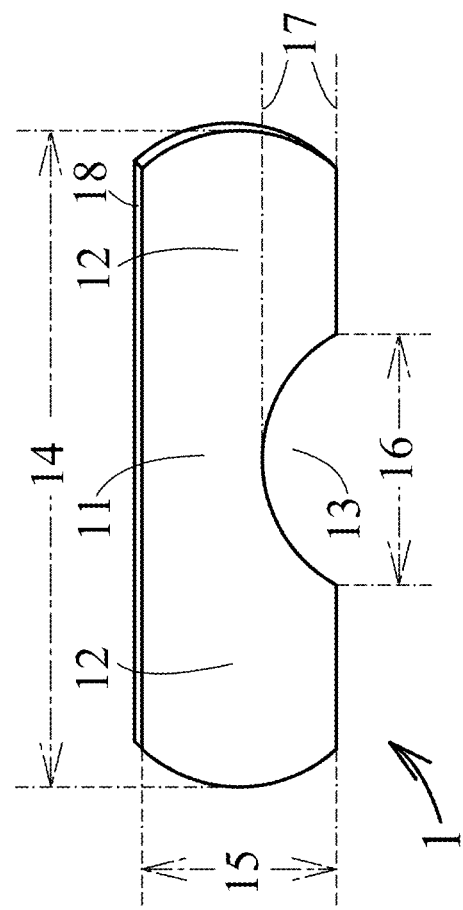
FIG. 1 is a perspective view from the upper-front-right, illustrating a preferred embodiment of the nose protection invention.

The nose protection apparatus 1 of the invention is illustrated in a preferred embodiment by FIG. 1. As can be seen, the nose protection apparatus 1 comprises a narrowed center bridge region 11 along with two outer protective regions 12 integrated as a single-piece unit, and a nasal bridge clearance cutout 13 beneath the center bridge region 11. As illustrated in FIG. 1, for example not limitation, the upper boundary of nose protection apparatus 1 forms a substantially straight line, the lower boundary also forms a substantially straight line but is broken in the center by the nasal bridge clearance cutout 13, and the side boundaries preferably have rounded contours. These features taken as a whole are designed to provide a comfortable fit over the user's nose 2 (see FIG. 2) as well as good nasal protection when the invention is in use.

Recognizing that humans have noses of varied shapes and sizes, the following dimensions are preferred for the average adult nose, with a variety of ranges to accommodate larger-than-average and smaller-than-average noses: The preferred overall width 14 of nose protection apparatus 1 is from 1.2" to 2.8", and more preferably from 1.6" to 2.4", and most preferably approximately 2". The preferred overall height 15 of nose protection apparatus 1, substantially scaling with the foregoing ranges for width 14, is from 0.375" to 0.875", and more preferably from 0.5" to 0.75", and most preferably from approximately 0.625". The preferred cutout width 16 of the nasal bridge clearance cutout 13 is from 0.375" to 1.125", and more preferably from 0.5625" to 0.9735" and even more preferably from 0.675" to 0.825", and most preferably approximately 0.75", also substantially scaling with the foregoing. And the preferred cutout depth 17 of the nasal bridge clearance cutout 13 is from 0.125" to 0.375", and more preferably from 0.1875" to 0.3125", and even more preferably from 0.225" to 0.275", and most preferably 0.25", also substantially scaled with the foregoing. Finally, the preferred thickness 18 of the nose protection apparatus 1 is from 0.02" to 0.05", and more preferably from 0.0225" to 0.0375", and most preferably approximately 0.025". For children, all physical dimensions other than the thickness 18 are reduced by approximately 50%.

In its preferred embodiment, the nose protection apparatus 1 is fabricated from silicone material, which includes but is not limited to silicone, silicone gel and/or silicone rubber, with the thickness 18 ranging as just reviewed, and a durometer hardness preferably from 5 to 20, more preferably from 7.5 to 15, even more preferably from 9 to 12, and most preferably approximately 10. Importantly, the nose protection apparatus 1 omits any added adhesives, so that all adhesion of the nose protection apparatus 1 to the nose 2 is effectuated entirely from the material properties of the silicone and its aforementioned durometer hardness. Specifically, it is an inherent property of silicone that it will naturally adhere to other materials, including in the present case, human skin. This adhesion will vary depending on the durometer hardness, and the thickness, both of which impact flexibility. Moreover, the skin on the human nose is sensitive, so that strong adhesives can tear or irritate the skin or do other damage. At the same time, too weak of an adhesion to the nose 2 will prevent the nose protection apparatus 1 from staying put on the nose 2 in order to carry out its intended function, and cause it to fall off. It is also important that the nose protection apparatus 1 flex to contact the nose, rather than exert any pull to flex the nose such as do the snore strips. Thus, the nose protection apparatus 1 omits any sort of structural elements e.g. ribs which would operate to straighten the nose protection apparatus 1, to pull the skin outside the nostrils apart, and to widen the nostrils once the nose protection apparatus 1 has adhered to the nose.

Accordingly, it was found during fabrication and testing of experimental prototypes that the spatial configuration shown in FIG. 1, in combination with the material being silicone with the foregoing thickness 18 and durometer hardness ranges, ideally optimize the natural adhesive properties of the silicone so as to provide necessary adhesion to the facial area of the nose 2, without over-adhering which can damage the nasal skin, all while flexing sufficiently to cover the necessary regions of the nose and adjacent face to perform the protective functions of the nose protection apparatus 1.

Other characteristics of the silicone material which were found to be optimal during experimental testing are the following, all within ranges of ±50%, more preferably ±25%, even more preferably ±10%, and most preferably approximately the numbers shown: tensile strength: 370 psi; elongation: 963%; tear B: 86 ppi. During production of these optimized prototypes, curing was at 177° C. The preferred finish is matte, and it is preferred for best cosmetic appearance that the color of the silicon material be either translucent or transparent. It will be appreciated that silicone with the aforementioned characteristics is hypoallergenic and non-toxic.

Figure 2:
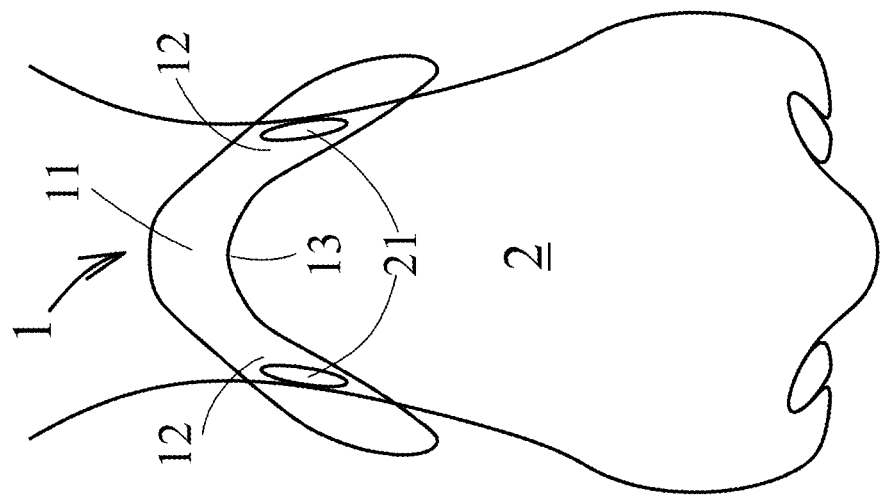
FIG. 2 is a front view illustrating the nose protection invention in use to protect the user's nose from pressure caused by eyewear pads.

FIG. 2 illustrates the method for using the nose protection apparatus 1 to protect a human nose 2 from prolonged pressure from the eyewear nose pads, bridge or frame. Prior to putting on eyewear such as a pair of glasses, the user first takes the nose protection apparatus 1, and with the nasal bridge clearance cutout 13 facing down, places the nose protection apparatus 1 over the bridge of the nose. The user then flexes the silicone material with durometer hardness and thickness 18 reviewed above, about the nose 2 as illustrated, so that the entire underside surface of the nose protection apparatus 1 contacts nose and adjacent facial regions as illustrated. Most importantly, at this point in the process the two outer protective regions 12 are placed to cover the skin over the two nasal bones. Then, the user places the glasses (not shown) over his or her eyes in the usual manner. And when the nose pads of the glasses come to rest upon the user's nose 2, these two outer protective regions 12 of the nose protection apparatus 1 will intercede so that the nose pads end up in contact with the contact regions 21 of the nose protection apparatus 1, or the eyewear bridge end up in contact with the contact region 11, rather than with the user's nose 2.

In this configuration of FIG. 2, the nose protection apparatus 1 a) dissipates the pressure of the eyewear contact points, b) cushions the nose, c) prevents abrasion to the nose from movement of the eyewear and d) because of the natural adhesion of silicone with multiple type of materials, counteracts the tendency of glasses to slide down the nose. Because it is entirely separate from the eyewear itself, the nose protection apparatus 1 can be used and is compatible with all kinds of eyewear to ameliorate pressure points and abrasion from eyewear.

In essence, the nose protection apparatus 1 is worn over the bridge of the nose like a saddle, as is seen in FIG. 2. Because the nose protection apparatus 1 as illustrated in FIG. 1 is horizontally symmetric and because both sides of the silicon are identical (again, importantly, no adhesives are employed beyond the natural adhesion of the silicon), the nose protection apparatus 1 can be placed and worn with either side in contact with the nose. Vertically, however, the nasal bridge clearance cutout 13 is placed to face down, and the narrowed center bridge region 11 joins the two outer protective regions 12 across the bridge of the nose where protection can be provided for the eyewear bridge if needed, and the clearance cutout 13 is designed to most comfortably mate with the natural contours of the human nose.

Prior to distribution to a user/consumer, the nose protection apparatus 1 material is preferably manufactured with one or both sides backed by a thin plastic which provides additional rigidity and prevents one or both sides from adhering to other objects prior to use. The backing is then peeled off manually by the user prior to use. Once the backing is removed, the material of the nose protection apparatus 1 will naturally conform to the shape of the nose and adhere to the nose when placed and positioned manually on the nose. The eyewear is then positioned so that it sits over the nose protection apparatus 1 as shown in FIG. 2, with the nose pads situated on the contact regions 21.

Although the nose protection apparatus 1 is washable and durable and can be attached to many surfaces and removed without damaging the shape, condition or utility of the invention, it is anticipated the nose protection apparatus 1 may need to be replaced periodically as a result of loss, damage or deterioration. However, because this device is easy-to-manufacture in bulk at low cost, this ought not raise any barrier for consumer purchases, and so it may be desirable to contain several devices, not just one, in a single point-of-sale package.

The nose protection apparatus 1 is a gender-neutral nose bridge protector which can be used in conjunction with all types of eyewear. It is safe and simple to use, it naturally and permanently smoothes out over time and can completely reverse the dents on a person's nose caused by eyewear, without toxic injections or chemicals.

Although the preferred embodiment described above is illustrated with a specific shape and specific size ranges, any shape or material with the same ability to alleviate pressure points, cushion the nose, and inhibit eyewear slipping, would serve as a suitable alternative embodiment. For example, a user may cut the material to custom shapes for any preferred fit for that specific user, using, e.g., a pair of curved nail scissors. Therefore, as noted, the lengths and widths can be varied to accommodate varying nose sizes and shapes. The dimensions reviewed earlier are for adult noses; it is understood that smaller versions of the invention scaled down for children are also regarded as being within the scope of this disclosure and its associated claims. Children sizes are approximately half the dimensions of the adult sizes. Although the preferred thickness 18 is from 0.02" to 0.05", and more preferably from 0.0225" to 0.0375", and most preferably approximately 0.025", this can also be varied by doubling the product itself, i.e., by layering two nose protection apparatuses 1 together. Also, the foregoing durometer hardness preferably from 5 to 20, more preferably from 7.5 to 15, even more preferably from 9 to 12, and most preferably approximately 10, is selected to optimize the flexibility and the adherent qualities of the silicone material. The invention can also be increased in thickness to add cushioning ability by positioning two or more of them overlapping each other. Although the preferred embodiment is translucent or transparent because it is expected that most users, cosmetically, will want the nose protection apparatus 1 not be visible to a casual observer, it is also understood that some users may wish to have nose protectors 1 in a variety of colors as a "fashion accessory."

Again, the nose protection apparatus 1 is a hypo-allergenic, non-toxic silicone nose protector/defender. Due to its physical qualities as reviewed, it conforms to the shape of and adheres to the nose, without pulling and without added adhesives which themselves can damage the sensitive nasal skin. It is easily applied and easily peeled-off while retaining its shape and condition. The nose protection apparatus 1 is washable and reusable. When used it significantly or totally eliminates the dents on the nose caused by nose pads, bridges or frame from all eyewear. Because of the inherent natural adhesion of silicone, the nose protection apparatus 1 inhibits all types of eyewear from sliding down the nose. The nose protection apparatus 1 is used with reading glasses, prescription glasses, sunglasses and safety glasses.

The method of manufacturing nose protection apparatus 1 is very simple and straightforward. In a preferred method, one simply prepares a silicone sheet with the appropriate thickness and other material characteristics disclosed above, then cuts individual nose protection apparatuses 1 from the sheet in the configuration of FIG. 1 with the dimensions and other layout characteristics disclosed and illustrated.

The knowledge possessed by someone of ordinary skill in the art at the time of this disclosure, including but not limited to the prior art disclosed with this application, is understood to be part and parcel of this disclosure and is implicitly incorporated by reference herein, even if in the interest of economy express statements about the specific knowledge understood to be possessed by someone of ordinary skill are omitted from this disclosure. While reference may be made in this disclosure to the invention comprising a combination of a plurality of elements, it is also understood that this invention is regarded to comprise combinations which omit or exclude one or more of such elements, even if this omission or exclusion of an element or elements is not expressly stated herein, unless it is expressly stated herein that an element is essential to applicant's combination and cannot be omitted. It is further understood that the related prior art may include elements from which this invention may be distinguished by negative claim limitations, even without any express statement of such negative limitations herein. It is to be understood, between the positive statements of applicant's invention expressly stated herein, and the prior art and knowledge of the prior art by those of ordinary skill which is incorporated herein even if not expressly reproduced here for reasons of economy, that any and all such negative claim limitations supported by the prior art are also considered to be within the scope of this disclosure and its associated claims, even absent any express statement herein about any particular negative claim limitations.

Finally, while only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

I claim:

1. A nose protection apparatus for protecting a human nose from prolonged contact between eyewear contact components and a human nose, said apparatus comprising:
   a center bridge region and two outer protective regions joined by said center bridge region all forming a flat sheet of uniform thickness within the same geometric plane, omitting any protrusions and omitting any recesses, fabricated from a silicone material into an integral unit;
   a nasal bridge clearance cutout beneath said center bridge region;
   omitting any added adhesives, wherein all adhesion properties of said apparatus for conforming and adhering to the bridge and sides of a user's nose are inherent to material properties of said silicone material;
   omitting any structural elements for straightening said apparatus for widening the user's nostrils;
   a width selected from the width group consisting of: an adult width from 1.2" to 2.8"; and a child width from 0.6" to 1.4";
   a height selected from the height group consisting of: an adult height from 0.375" to 0.875"; and a child height from 0.1875" to 0.4375";
   a thickness from 0.02" to 0.05"; and
   a durometer hardness from 5 to 20; wherein:
   said apparatus is rendered flexible by said thickness and said hardness; and
   said thickness and said hardness enable said nose protection apparatus to be flexed to rest said center bridge region upon a bridge of the user's nose and to rest said two outer protective regions upon sides of the user's nose.

2. The apparatus of claim 1, said silicone material selected from the material group consisting of at least one of: silicone; silicone gel; and silicone rubber.

3. The apparatus of claim 1, further comprising a nasal bridge clearance cutout beneath said center bridge region comprising a cutout width thereof from 0.375" to 1.125" and a cutout depth thereof from 0.125" to 0.375".

4. The apparatus of claim 1:
   said width selected from the width group consisting of: an adult width from 1.6" to 2.4"; and a child width from 0.5" to 0.75"; and
   said height selected from the height group consisting of: an adult height from 0.5" to 0.75"; and a child height from 0.25" to 0.375".

5. The apparatus of claim 4:
   said width selected from the width group consisting of: an adult width from of approximately 2"; and a child width of approximately 1"; and
   said height selected from the height group consisting of: an adult height of approximately 0.625"; and a child height of approximately 0.3125.

6. The apparatus of claim 1, said thickness being from 0.0225" to 0.0375".

7. The apparatus of claim 6, said thickness being approximately 0.025".

8. The apparatus of claim 1, said durometer hardness being from 7.5 to 15.

9. The apparatus of claim 8, said durometer hardness being from 9 to 12.

10. The apparatus of claim 9, said durometer hardness being approximately 10.

11. The apparatus of claim 1:
- said width selected from the width group consisting of: an adult width from of approximately 2"; and a child width of approximately 1";
- said height selected from the height group consisting of: an adult height of approximately 0.625"; and a child height of approximately 0.3125;
- said thickness being approximately 0.025"; and
- said durometer hardness being approximately 10.

12. The apparatus of claim 11, further comprising:
- a tensile strength of 370 psi ±25%;
- an elongation of 963%±25%; and
- a tear B of 86 ppi ±25%.

13. A method for protecting a human nose from prolonged contact between eyewear contact components and a human nose, comprising:
- prior to putting on eyewear, placing over a user's nose, a nose protection apparatus comprising a center bridge region and two outer protective regions joined by said center bridge region all forming a flat sheet of uniform thickness within the same geometric plane, omitting any protrusions and omitting any recesses, fabricated from a silicone material into an integral unit, said nose protection apparatus further comprising a nasal bridge clearance cutout beneath said center bridge region;
- flexing said nose protection apparatus so that said center bridge region rests upon a bridge of the user's nose and said two outer protective regions rest upon sides of the user's nose;
- conforming and adhering said nose protection apparatus to the user's nose bridge and sides using only adhesion and flexibility properties inherent to material properties of said silicone material, and omitting any added adhesives;
- not widening a user's nostrils, by omitting any structural elements for straightening said apparatus; wherein:
- a width of said nose protection apparatus is selected from the width group consisting of: an adult width from 1.2" to 2.8"; and a child width from 0.6" to 1.4";
- a height of said nose protection apparatus is selected from the height group consisting of: an adult height from 0.375" to 0.875"; and a child height from 0.1875" to 0.4375";
- a thickness of said nose protection apparatus is from 0.02" to 0.05"; and
- a durometer hardness of said nose protection apparatus is from 5 to 20;
- wherein said apparatus is rendered flexible by said thickness and said hardness.

14. The method of claim 13, further comprising selecting said silicone material from the material group consisting of at least one of: silicone; silicone gel; and silicone rubber.

15. The method of claim 13, further comprising providing a nasal bridge clearance cutout beneath said center bridge region comprising a cutout width thereof from 0.375" to 1.125" and a cutout depth thereof from 0.125" to 0.375".

16. The method of claim 13, wherein:
- said width is selected from the width group consisting of: an adult width from 1.6" to 2.4"; and a child width from 0.5" to 0.75"; and
- said height is selected from the height group consisting of: an adult height from 0.5" to 0.75"; and a child height from 0.25" to 0.375".

17. The method of claim 16, wherein:
- said width is selected from the width group consisting of: an adult width from of approximately 2"; and a child width of approximately 1"; and
- said height is selected from the height group consisting of: an adult height of approximately 0.625"; and a child height of approximately 0.3125.

18. The method of claim 13, wherein said thickness is from 0.0225" to 0.0375".

19. The method of claim 18, wherein said thickness is approximately 0.025".

20. The method of claim 13, wherein said durometer hardness is from 7.5 to 15.

21. The method of claim 20, wherein said durometer hardness is from 9 to 12.

22. The method of claim 21, wherein said durometer hardness is approximately 10.

23. The method of claim 13, wherein:
- said width is selected from the width group consisting of: an adult width from of approximately 2"; and a child width of approximately 1";
- said height is selected from the height group consisting of: an adult height of approximately 0.625"; and a child height of approximately 0.3125;
- said thickness is approximately 0.025"; and
- said durometer hardness is approximately 10.

24. The method of claim 23, wherein said nose protection apparatus further comprises:
- a tensile strength of 370 psi ±25%;
- an elongation of 963%±25%; and
- a tear B of 86 ppi ±25%.

* * * * *